US00PP14992P2

(12) United States Plant Patent
van Dijk

(10) Patent No.: US PP14,992 P2
(45) Date of Patent: Jul. 6, 2004

(54) ANTHURIUM ANDREANUM PLANT NAMED 'ANTHBNEM'

(50) Latin Name: *Anthurium andreanum L.*
Varietal Denomination: Anthbnem

(75) Inventor: Jan van Dijk, Bleiswijk (NL)

(73) Assignee: Anthura B.V. (NL)

( * ) Notice: Subject to any disclaimer, the term of this patent is extended or adjusted under 35 U.S.C. 154(b) by 0 days.

(21) Appl. No.: 10/612,053

(22) Filed: Jul. 3, 2003

(51) Int. Cl.[7] ..... A01H 5/00

(52) U.S. Cl. ..... Plt./365

(58) Field of Search ..... Plt./365

(56) References Cited

PUBLICATIONS

GTITM UPOVROM citation for 'Anthbnem' as per QZ PBR 011313; Aug. 13, 2001.*

* cited by examiner

*Primary Examiner*—Kent Bell
(74) *Attorney, Agent, or Firm*—Foley & Lardner

(57) ABSTRACT

A new and distinct cultivar of an *Anthurium andreanum* plant named 'Anthbnem', as described and illustrated, and particular characterized by the combined features of compact plant growth and early and very rich flowering; mini-type pot plant, maximum growth to an average of 40 cm; long and erect peduncle, flowers held well above the foliage; full plant habit due to shoot formation, lush plant due to straight but flexible flower and leaf petioles; dark green leaves, compact, durable with light green primary veins; red and very durable flowers, lastingness of the inflorescence up to one year; and large amount of flowers in relation to the amount of leaves, resulting in an excellent leaf to flower size ratio.

4 Drawing Sheets

Latin name of the genus and species of the plant claimed: *Anthurium andreanum L.*
Variety denomination: Anthbnem.

BACKGROUND OF THE INVENTION

'Anthbnem' is a new and distinct cultivar of Anthurium, botanically known as *Anthurium andreanum L.* The new cultivar is a product of a planned breeding program, and was obtained from a cross made during such a program in Bleiswijk, The Netherlands, in 1996.

The female or seed parent was a pink-colored Anthurium pot plant designated number 95-634-01 (unpatented). The male or pollen parent was an orange-colored flowering Anthurium pot plant designated number 95-532-02 (proprietary, unpatented). 'Anthbnem' was discovered and selected as a flowering plant within the progeny of the stated cross by the inventor, Jan van Dijk, in March, 1998 in a controlled environment in a glasshouse in Bleiswijk, The Netherlands.

Subsequent asexual reproduction by tissue culture at the same location has demonstrated that the combination of characteristics as herein disclosed for the new cultivar are firmly fixed and are retained through successive generations of asexual reproduction. The new cultivar reproduces true to type through successive generations of asexual reproduction.

BRIEF DESCRIPTION OF THE INVENTION

The following traits have been repeatedly observed and in combination distinguish 'Anthbnem' as a new and distinct cultivar:

1. Compact plant growth and early and very rich flowering;

2. Mini-type pot plant, maximum growth to an average of 40 cm;
3. Long and erect scape, inflorescences held well above the foliage;
4. Full plant habit due to shoot formation, lush plant due to straight but flexible inflorescence and leaf petioles;
5. Dark green leaves, compact, durable with light green primary veins;
6. Red and very durable inflorescences, lastingness of the inflorescence up to one year; and
7. Large amount of inflorescences in relation to the amount of leaves, resulting in an excellent leaf to inflorescence size ratio.

BRIEF DESCRIPTION OF THE DRAWINGS

The accompanying photographs, taken in Bleiswijk, The Netherlands, show typical 'Anthbnem' specimens.

FIG. 1 is a side-view of 'Anthbnem' showing the inflorescences held well above the leaf canopy.

FIG. 2 is a close-up of a 'Anthbnem' inflorescence showing the spathe and spadix with some pollen.

FIG. 3 is a close-up of 'Anthbnem' inflorescences at three different stages of development: from young on the left to old on the right. The youngest inflorescence has an unripe spadix (pistils and pollen are not visible yet). The inflorescence in the middle has a ripe spadix with some pollen. The spathe of the old inflorescence on the right becomes brown-red. Between the left and the right inflorescences is a difference in age of approximately 8 to 10 weeks.

FIG. 4 is a close-up of the top a young (left) and old leaf blade (right) showing the difference in leaf color. It also shows that the young leaf blades are more shiny then the old leaf blades.

DETAILED BOTANICAL DESCRIPTION

The following observations, measurements and values describe 60 week old plants grown in 17 cm containers, in Bleiswijk, The Netherlands, under greenhouse conditions, which closely approximate those generally used in horticultural practice.

Color references are made to The Royal Horticultural Society (R.H.S.) Colour Chart, except where general color terms of ordinary significance are used. The color references are approximate, as color depends to a degree on horticultural practices such as light level and degree of fertilization, among others. The color values were determined between 11:00 a.m. and 3:00 p.m. on Feb. 25, 2003, under 5000 lux natural light in a glasshouse in Bleiswijk, The Netherlands. The phenotype may vary significantly when grown under different conditions of temperature, light or other determining factors, without a change in genotype of the plant.

PROPAGATION

Asexual propagation by means of tissue culture and all subsequent propagation that flowered have been true to the original type in plant and flower characteristics.

PLANT DESCRIPTION

Approximately 55–60 weeks following division, 'Anthbnem' will reach a mature size of approximately 35 cm to 45 cm in height and approximately 35 cm to 45 cm in width in a 17 cm container. However, 'Anthbnem' can be easily grown to a smaller size for example 30 cm in height, when it is placed in a 14 cm container. The plant is compact.

LEAVES

Form: The leaf blade is elliptical-cordate with an acuminate tip and a cordate base. The margin is entire. The leaf blade angle with the petiole is between 100 and 150 degrees. 'Anthbnem' makes slightly larger leaf blades as it ages. 'Anthbnem' also produces some axillary shoots with small leaf blades. Therefore, a wide range in leaf blade length and width is found on each plant. The minimum leaf blade length is approximately 4 cm and the maximum leaf blade length is approximately 18 cm. The minimum leaf blade width is approximately 3 cm and the maximum leaf blade width is approximately 11 cm.

Texture: The leaf blades are shiny, leatherly and thick. The mature leaf blades are weakly cupped. The young leaf blades have more shine than the old leaf blades.

Veins: The mid-vein and primary veins (the veins which radiate out from the juncture of the petiole and leaf) protrude at the underside of the leaf blade. In older leaf blades (approximately more than 4 weeks) the green color of the veins at the upper surface (RHS 146B) and the lower surface (RHS 144D) of the mid-vein and primary veins contrast with the green color of the surface of the leaf blade.

Leaf blade-color: Young leaf blade (approximately maximum 4 weeks old) upper and lower surface is dark green (RHS 147A). On the old leaf blade (approximately more than 4 weeks) the upper surface is dark green (RHS 147A) and the lower surface is light green (RHS 137C).

Lobes: A leaf blade has two small lobes extending past the petiole. The distance from the petiole and leaf juncture to the highest point on the lobes of mature leaf blades (width 11 cm, length 18 cm) ranges approximately from 2 to 3 cm.

Petiole: The color of the petiole of an old leaf blade is green (RHS 147B). The color of the petiole of a young leaf blade is brown-red (RHS 178B). The cross section of the petiole is round and the diameter is approximately 3 mm. The length of the petiole varies with age. The petiole of an early leaf blade is 3 cm in length, and a mature leaf petiole is approximately 25 cm in length. The color of the cataphyls surrounding the petioles is grey-green (RHS 148A) with a reddish tip (RHS 180A).

SPATHE

Buds: The spathe is tightly rolled around the spadix and extrudes from the peduncle sheath. After the spathe is fully open the scape elongates for a few more centimeters.

Size: The completely developed spathe of a 35 cm tall plant is approximately 7 cm to 8 cm long and approximately 9 cm to 10 cm wide.

Color: When the spathe is just fully open, the upper surface is red (RHS 45B) and the lower surface is also red (RHS 47A). Approximately 7 to 8 weeks after the opening, the spathe starts discoloring to brown-red (RHS 183A). The red color slightly turns into brown.

Arrangement: The spathe angle with the scape is between 100 and 130 degrees. The spathe stand on a straight wiry scape approximately 5 cm to 8 cm above the foliage. The scape cross-section is round and the diameter approximately 2 mm to 3 mm, depending on the age of the plant. The scape is erect and it's length on the plant depends on the age. It ranges from approximately 15 to 25 cm. The color of the scape ranges from light green RHS 137D at the base of the scape to red-purple RHS 60A at the top.

Shape: The spathe is ovate with a mucronate tip and a cordate base. The margin is entire. A just fully opened spathe is slightly cup-shaped. The edges of the spathe stay upwards. All the flowers tend to be asymmetrical, having one smaller and one bigger lobe.

FLOWERING TIME

One small untreated tissue culture plant of approximately 2 cm tall will flower, depending on season, after approximately 15 to 16 months when approximately 2 to 3 inflorescences will appear. More inflorescences appear after some weeks so that a full flowering and salable plant can have 8 to 14 red inflorescences. Smaller inflorescences may occur on less mature growth.

REPRODUCTIVE ORGANS

Size: The spadix, with approximately 200 flowers produced per spadix, measures approximately 3 to 4 cm in height and 0.2 cm in diameter. The length of the spadix is shorter than the length of the spathe. The spadix is a little columnar. The width of a mature spadix that is approximately 4 cm long is approximately 7 mm at the base and approximately 6 mm at the top. The spadix angle with spathe is approximately 50 to 70 degrees.

Color: At the time the spathe unrolls the spadix is fully unripe. Later as the spadix matures, pistils become visible and pollen is produced. An unripe spadix is orange-brown (RHS 180B) and a ripe spadix is pink (RHS 65B). As the spadix matures (from base to tip) it becomes fully pink (RHS 65B), later turning to green (RHS 137B).

Stamens: Anthers and filaments are not clearly visible on the spadix.

Pollen: A large amount does appear and has a white color.

Pistil: An unripe pistil is orange-brown (RHS 180B) and a ripe pistil is pink (RHS 65B). The pistil protrudes from the spadix and is surrounded by a very tiny band, darker than the spadix.

ROOTS

Light pinkish-white roots with smaller hairy laterals. The root-tips are yellow.

DISEASE/PEST RESISTANCE

No known resistance and/or susceptibility to diseases and pests.

I claim:

1. A new and distinct *Anthurium andreanum* plant named 'Anthbnem', as herein described and illustrated.

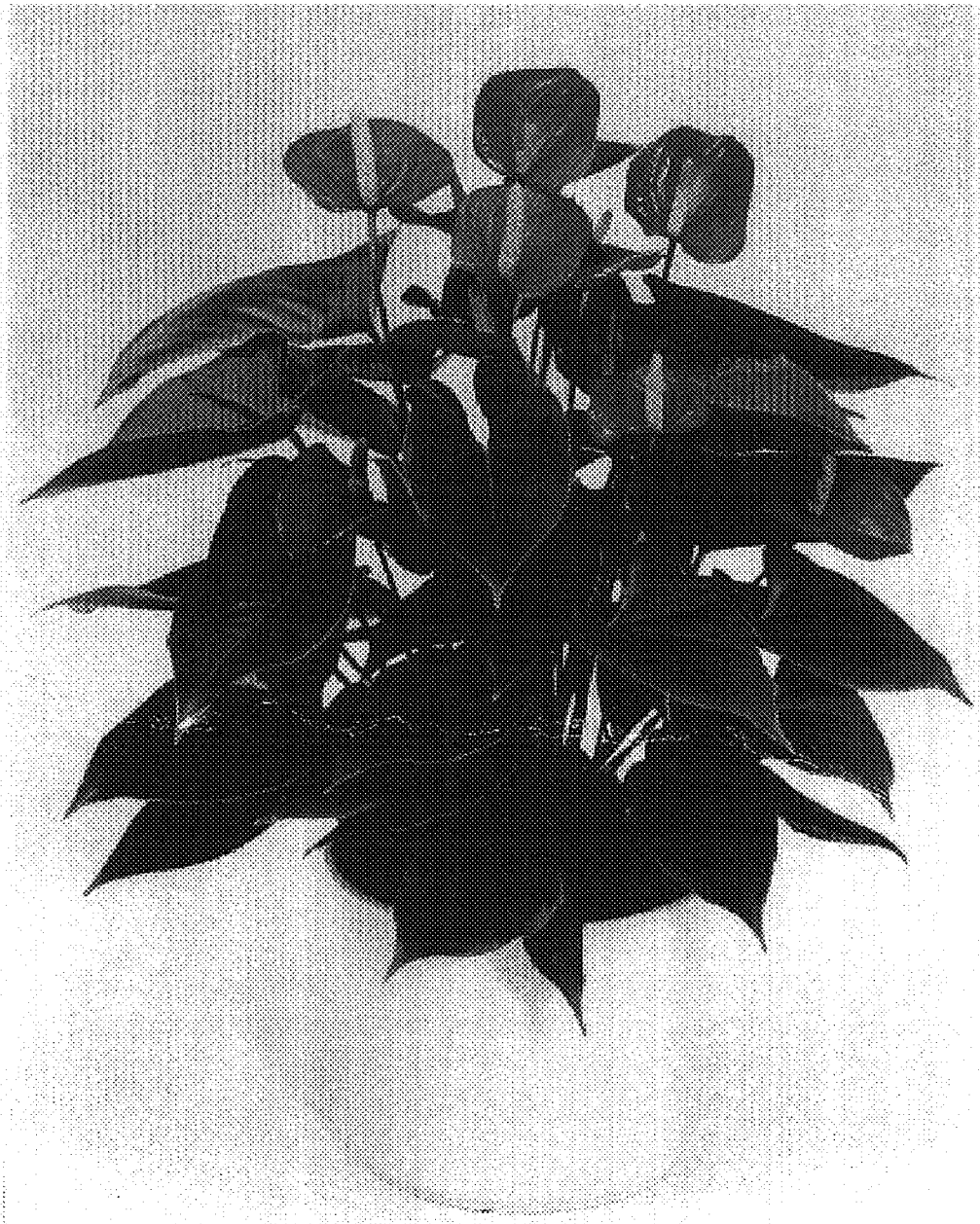

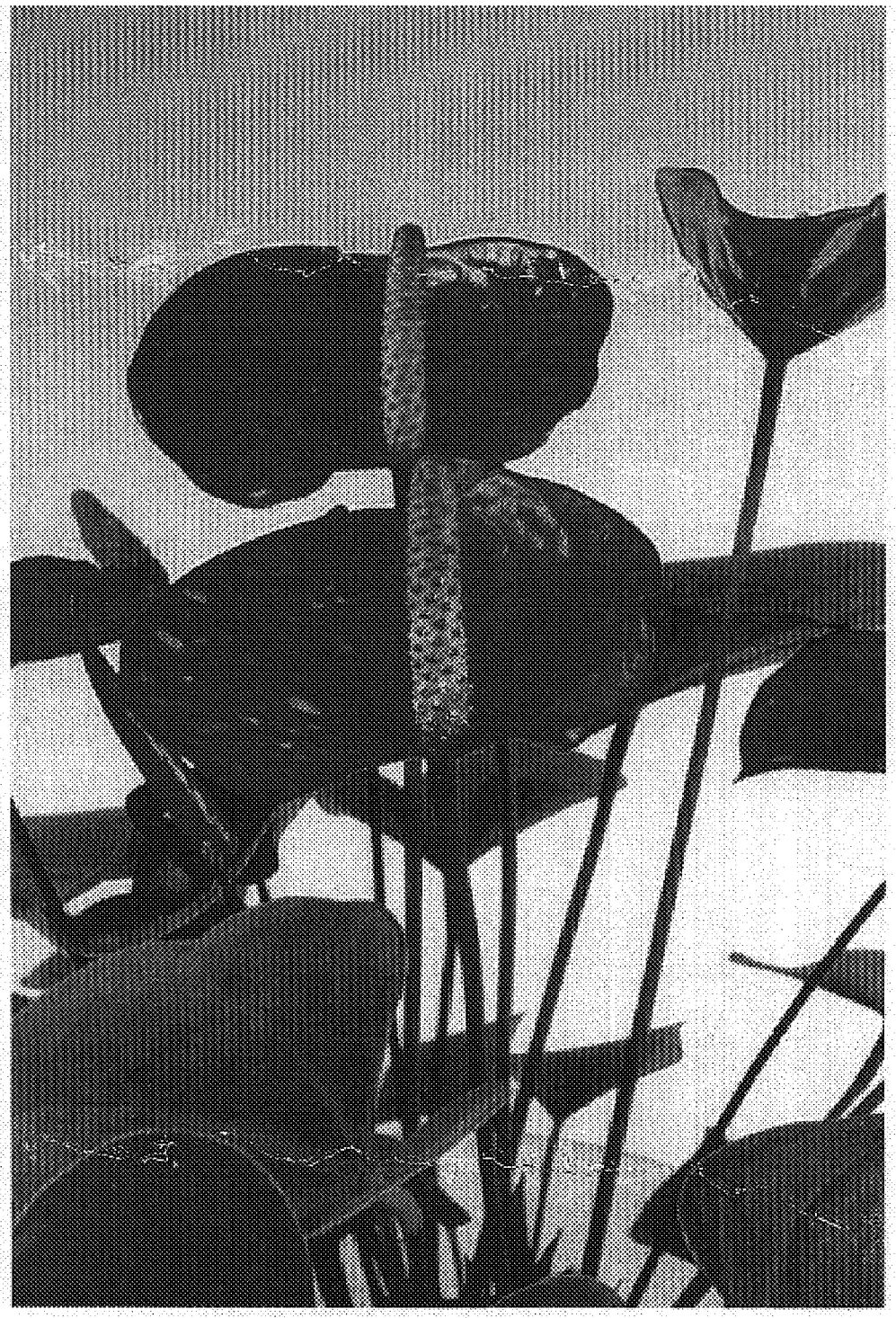

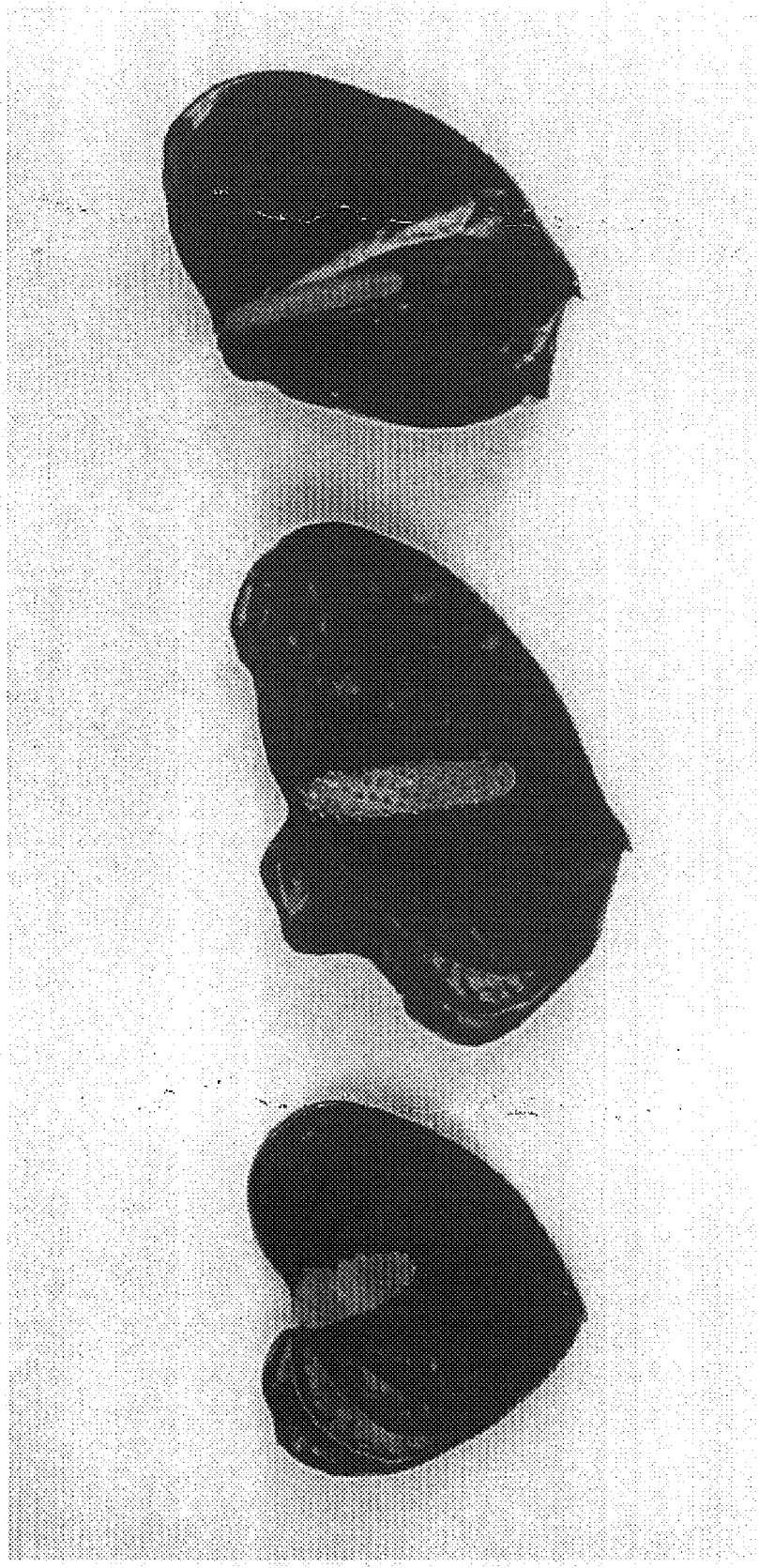

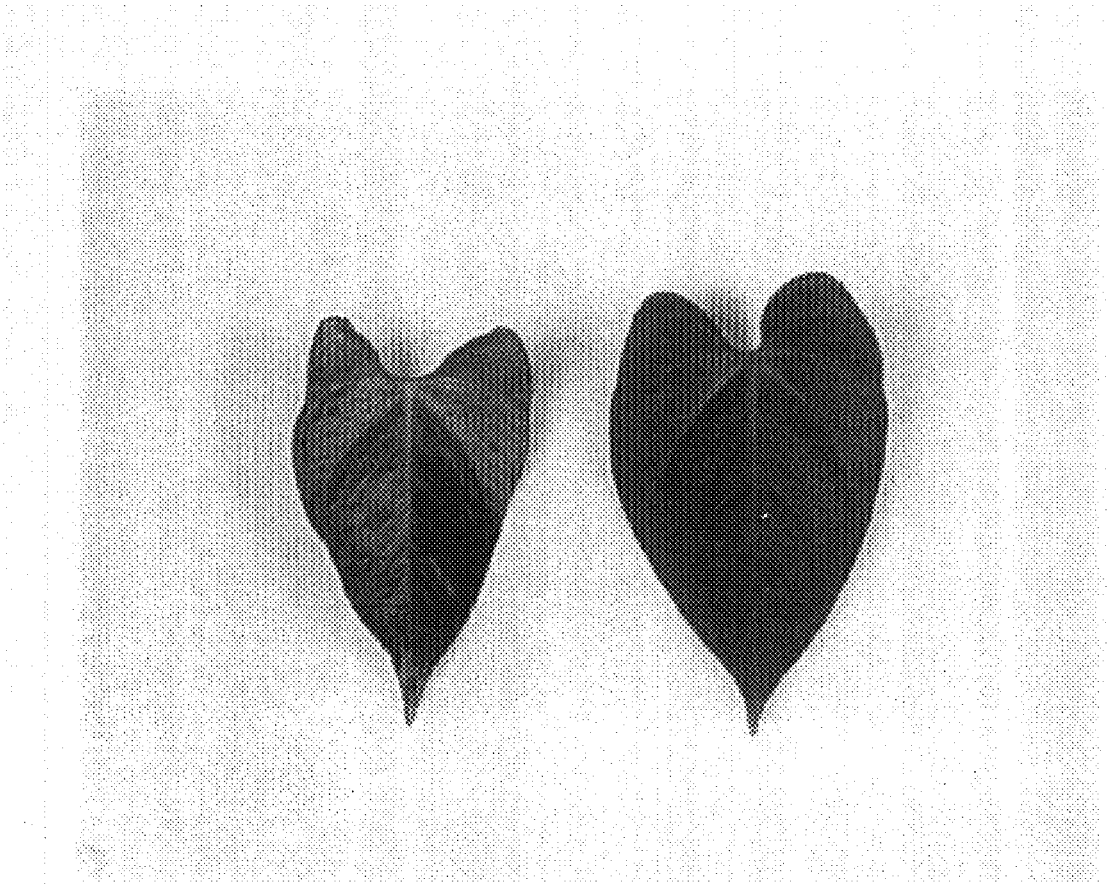

* * * * *